United States Patent
Paul et al.

(10) Patent No.: US 6,733,526 B2
(45) Date of Patent: May 11, 2004

(54) METHOD OF IMPROVING ADHERENCE AND CENTERING OF INTRA-CORNEAL IMPLANTS ON CORNEAL BED

(75) Inventors: Marlene L. Paul, Laguna Niguel, CA (US); Robert Glick, Lake Forest, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 18 days.

(21) Appl. No.: 10/132,465

(22) Filed: Apr. 25, 2002

(65) Prior Publication Data

US 2003/0204252 A1 Oct. 30, 2003

(51) Int. Cl.[7] ................................................ A61F 2/14
(52) U.S. Cl. ..................................................... 623/5.11
(58) Field of Search ................ 623/4.1, 5.11, 623/5.12, 5.16, 901, 920

(56) References Cited

U.S. PATENT DOCUMENTS

| | | |
|---|---|---|
| 4,134,160 A | 1/1979 | Bayers |
| 4,327,725 A | 5/1982 | Cortese et al. |
| 4,597,965 A | 7/1986 | Holly |
| 4,655,774 A | 4/1987 | Choyce |
| 4,709,996 A * | 12/1987 | Michelson .................. 359/665 |
| 4,834,748 A | 5/1989 | McDonald |
| 4,840,754 A | 6/1989 | Brown et al. |
| 5,019,097 A | 5/1991 | Knight et al. |
| 5,123,921 A | 6/1992 | Werblin et al. |
| 5,389,383 A | 2/1995 | Huth |
| 5,433,745 A | 7/1995 | Graham et al. |
| 5,630,884 A | 5/1997 | Huth |
| 5,632,773 A | 5/1997 | Graham et al. |
| 5,719,110 A * | 2/1998 | Cook .......................... 510/112 |
| 6,007,510 A | 12/1999 | Nigam |
| 6,030,416 A | 2/2000 | Huo et al. |
| 6,346,560 B1 | 2/2002 | Nandu et al. |
| 2003/0045930 A1 * | 3/2003 | Nguyen ..................... 623/5.11 |

FOREIGN PATENT DOCUMENTS

WO  0006223  2/2000

* cited by examiner

Primary Examiner—David H. Willse
Assistant Examiner—William H. Matthews
(74) Attorney, Agent, or Firm—Peter Jon Gluck

(57) ABSTRACT

A partially hydrated lens is provided for implantation into a cornea. The partially hydrated lens has a water content less than the water content of the cornea, resulting in an osmotic pressure differential between the lens and the cornea which improves adhesion between the lens and the corneal tissue. It also causes the lens to expand and flatten when implanted, and to [naturally center itself while flattening.] In the preferred embodiment of the invention, the lens is maintained in its partially hydrated state by storage in a hypertonic hydration medium.

19 Claims, 2 Drawing Sheets

METHOD OF IMPROVING ADHERENCE AND CENTERING OF INTRA-CORNEAL IMPLANTS ON CORNEAL BED

BACKGROUND OF THE INVENTION

The present invention relates to methods of improving the adherence and/or centering of intra-corneal implants to the corneal bed. More particularly, the invention relates to methods for pre-treating intra-corneal implants so that the implants, after being placed in contact with the cornea, effectively self-center and adhere to the corneal bed, for example, without sutures.

Various treatments are known for correcting corneal refractive errors. The use of lasers, for instance, to reshape the cornea by removing corneal tissue, has become increasingly popular in recent years. However, the removal of tissue can result in loss of the structural integrity of the cornea, and can also cause bulging.

Furthermore, once corneal tissue has been removed, it can not easily be restored. Thus, laser vision correction is substantially irreversible.

The need for a reversible treatment which does not adversely affect the structural integrity of the cornea has led to the use of intra-corneal implants, which do not require the removal of tissue. Instead, a single small incision is made in the cornea to make a flap or hinge, which is then folded back to expose the middle layer of corneal tissue known as the stromal bed. A corrective lens, typically formed of hydrogel material, is placed on the stromal layer. Then the flap is returned to its initial position and smoothed over the lens.

Various techniques have been used for affixing the lens to the cornea once it has been embedded. In some cases, sutures are used. Other techniques eliminate sutures, but rely on a very close match between the curvature of the lens and the curvature of the recipient's eye. None of these techniques have been entirely satisfactory, resulting in some slippage between the lens and the cornea, and improper positioning in the eye.

Therefore, it would be advantageous to develop methods and apparatus for enhancing the adherence and/or centering of intra-corneal implants on the corneal bed.

SUMMARY OF THE INVENTION

New apparatus and methods for treating intra-corneal implants to enhance centering and adherence have been discovered. The present invention addresses one or more of the concerns of the prior art systems, such as those noted above. Moreover, the present methods are straightforward, relatively easy to produce, use and practice, and provide substantial benefits to both the surgeon implanting the intra-corneal implants, and the patient receiving the implants.

In one broad aspect of the invention, a partially hydrated lens is provided for implantation into the stroma of a cornea. The partially hydrated lens comprises an amount of fluid selected to create an osmotic pressure gradient with respect to fluids in the cornea. This osmotic pressure gradient enhances adhesion of the lens to the cornea. In addition, the lens is configured to expand and flatten as it absorbs water from the cornea, naturally centering itself prior to flattening.

In another broad aspect of the invention, the partially hydrated lens is packaged in a hypertonic hydrating solution.

In still another broad aspect of the invention, a method of treating refractive errors in a cornea comprises implanting a partially hydrated lens formed of a hydrophilic polymeric material lens into the cornea, wherein the osmotic pressure differential between the partially hydrated implant and the cornea causes the implant to adhere to the cornea. In one embodiment, the step of implanting the partially hydrated lens is preceded by a step of wetting a pre-hydrated lens with a hypertonic aqueous hydration medium. In another embodiment, the step of implanting the partially hydrated lens is preceded by a step of drying a more hydrated lens.

Each and every feature described herein, and each and every combination of two or more of such features, is included within the scope of the present invention provided that the features included in such a combination are not mutually inconsistent.

These and other broad aspects and advantages are set forth in the following detailed description and claims, particularly when considered in conjunction with the accompanying drawings in which like parts bear like reference numerals.

DESCRIPTION OF THE PREFERRED EMBODIMENTS

Figure 1:
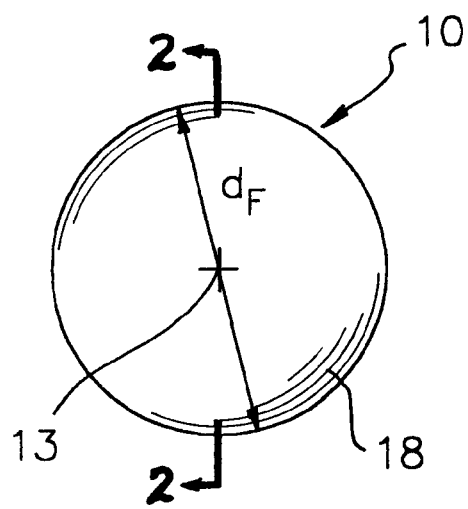
FIG. 1 is a front view of a lens according to the present invention in its equilibrium state.
Figure 2:
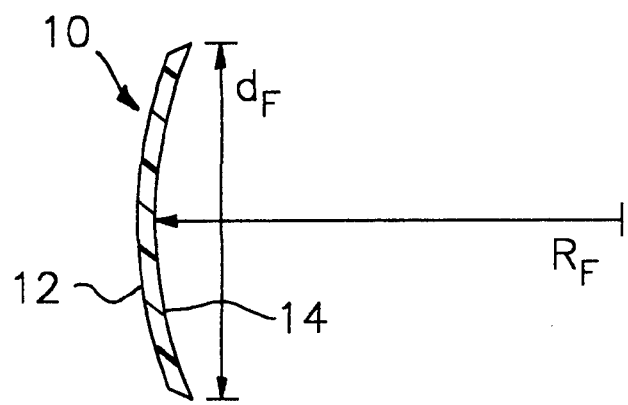
FIG. 2 is a transverse sectional view taken through line 2—2 of FIG. 1.

Referring now to the drawings, FIGS. 1 and 2 show an exemplary lens or intra-corneal implant 10 structured to be implanted in a cornea, preferably in the stroma of the cornea. For the purposes of this disclosure, the terms "lens" and "implant" are used substantially interchangeably, with "lens" generally being used to refer to the lens 10 in its pre-implanted state, and "implant" being used to refer to the lens 10 after implantation. Also for the purposes of this disclosure, the term "cornea" is used somewhat interchangeably with "stroma", and with the implicit understanding that, while the stroma is the presently preferred location for an intra-corneal implant, other layers of the cornea may also be suitable.

The lens 10 is illustrated as circular in plan, with a diameter $D_F$ and radius of curvature $R_F$. The lens 10 includes a convex anterior surface 12 approaching the optical axis 13, and a concave posterior surface 14. However, the principles of the invention may also be applied to lenses of other shapes and curvature.

The lens 10 may be made of any material, preferably a hydrophilic material, that swells when wetted with an aqueous liquid medium, has a suitable index of refraction, and is known to be compatible with corneal tissue. In a preferred embodiment, the lens 10 comprises a composition including a hydrophilic polymeric material, preferably a hydrogel-forming polymeric material, and water.

Specific examples of useful hydrophilic polymeric materials include polymers derived in whole or in part from monomers which possess an unsaturated vinyl or allyl group and produce polymers which exhibit hydrophilicity. Such monomers include, but are not limited to, acryl type monomers, methacryl type monomers, unsaturated amide type monomers, diene type monomers, and triene type monomers which meet the requirements mentioned above. Typical examples of such monomers include (meth) acrylamides, N-methyl(meth)acrylamides, N,N-dimethyl (meth)acrylamides, N,N-methylethyl(meth)acrylamides, N,N-diethyl(meth)acrylamides, (meth)acrylicacids, 2-hydroxyethyl(meth)acrylates, N,N-dimethylaminoethyl (meth) acrylates, N,N-diethyl-amino-ethyl(meth)acrylates, N-vinylpyrrolidone, p-styrene sulfonic acid, vinyl sulfonic acid, 2-methyacryloyloxethyl acid, 2-acrylamide-2methylpropane sulfonic acid, and the like, and mixtures thereof.

In a prior art procedure, a pre-hydrated lens is wetted to a final hydrated state prior to implantation in the stroma of the cornea. This prior art wetting procedure typically consists of dipping or soaking and storing the lens in an isotonic hydration medium, which is understood in the art to mean a solution having an osmotic pressure approximately equal to fluids in the cornea. In the final hydrated state, also defined here as the equilibrium state, there is substantially no osmotic pressure differential between the fluids in the lens 10 and the fluids in the stroma into which the lens is to be implanted.

In the method according to the present invention, the lens 10 is only partially hydrated before implantation in the cornea. The degree to which the pre-hydrated lens should be hydrated prior to implantation can be determined in a variety of ways. One way is to consider the curvature of the lens. In its final hydrated state, the lens should have a curvature substantially conforming to the uniformly curved central area of a patient's stroma. Thus, the lens in the partially hydrated state should be more steeply curved than the stromal bed, yet not so steeply curved as to cause excessive discomfort in the patient when it is first implanted.

Another way of determining the extent of hydration is to consider imbibition pressure, which is defined as the tendency of the lens to absorb water. The partially hydrated lens should have an imbibition pressure higher than the osmotic pressure of stromal fluids, while the lens in its final, or equilibrium, state should have an imbibition pressure approximately equal to the osmotic pressure of stromal fluids. Thus, the lens 10 substantially ceases to absorb fluid from a cornea having normal fluid levels when the lens 10 reaches its equilibrium state, thereby reducing the possibility of dry eye in a normal patient.

The hydration level can also be expressed in terms of the colloidal osmotic pressure of fluids in the lens material. When the lens 10 is in its partially hydrated state, the colloidal osmotic pressure of fluids in the lens should be less than the osmotic pressure of fluids in the stroma, so that an osmotic pressure gradient is established, which enhances adhesion of the implant to the stroma. In the equilibrium state, the colloidal osmotic pressure of fluids in the lens should be approximately equal to the osmotic pressure of the stromal fluids.

Figure 6:
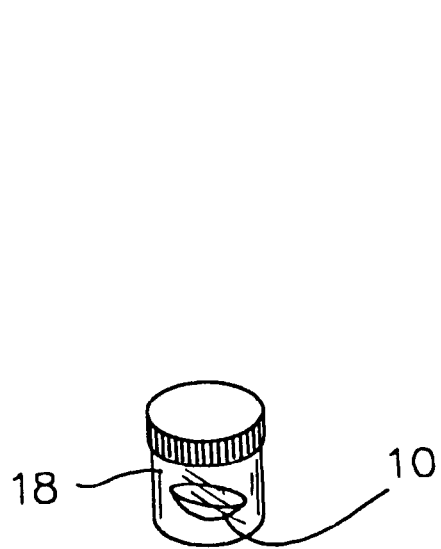
FIG. 6 is a perspective view showing a packaging arrangement including the lens of the present invention.

In one embodiment of the invention, the lens 10 is maintained in the partially hydrated state by soaking and storage in a hypertonic hydration medium 18, which is understood in the art to mean a solution having an osmotic pressure greater than fluids in the cornea. For the sake of convenience, the partially hydrated lens 10 is preferably supplied to the ophthalmic surgeon pre-packaged with the hypertonic hydration medium 18. This relieves the surgeon and/or technicians of the need to hydrate the lens before surgery, and to determine whether the proper degree of hydration has been achieved. The packaging arrangement may comprise any suitable sealed vessel, such as a vial 16, containing the partially hydrated lens suspended in the hydration medium 18, as shown in FIG. 6.

The hydration medium may be selected from any suitable material effective to maintain the lens 10 in the desired partially hydrated state. Advantageously, the hydration medium is an aqueous-based liquid. Preferably, the hydration medium comprises an ophthalmically acceptable aqueous carrier, such as sterile purified water, to which a tonicity adjusting agent has been added. Suitable such agents include alkali metal halides, phosphates, hydrogen phosphate, and borates. Preferred are sodium chloride, potassium chloride, sodium phosphate monobasic and sodium phosphate dibasic and combinations thereof. The amount of the tonicity adjusting agent needed to achieve the desired hydration of the lens 10 can vary greatly depending on such properties as the permeability and the ratio of the water diffusion coefficient to the ion diffusion coefficient of the lens material. It can also vary based on the presence of other components in the carrier, including stabilizers, buffering agents, disinfectants, pH adjusters, and the like, all of which would be determined by the specific type of lens and the needs of the individual patient. Accordingly, there is no upper or lower critical limitation upon the amount of the tonicity adjusting agent. The required quantity to be employed in the present invention can be determined clinically by those skilled in the art.

In the presently preferred embodiment, the hydration medium is an aqueous solution having an osmotic pressure which is higher than the osmotic pressure of fluids in the cornea. Although the hydration medium is preferably hypertonic, the tonicity of the hydration medium should not be so high as to cause dry eye or other detrimental effects when placed in a cornea having normal fluid levels. Again, the maximum desirable tonicity will vary depending on numerous factors, but can be readily ascertained by a skilled practitioner of the ophthalmic arts.

Figure 3:
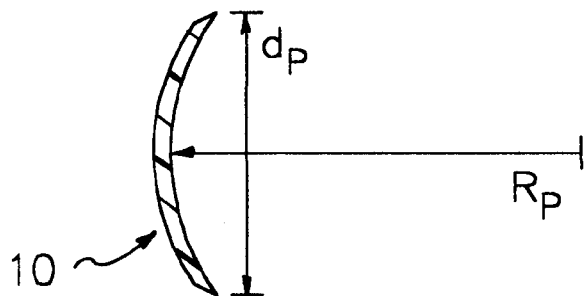
FIG. 3 is a transverse sectional view, similar to FIG. 2, showing the lens according to the present invention in a partially hydrated state.

FIG. 3 shows the lens 10 in its partially hydrated state, just prior to implantation in the cornea. The partially hydrated lens 10 has a generally spherical surface, but has a smaller diameter $d_P$ and a smaller radius of curvature $R_P$ than the lens 10 in its final state. For purposes of illustration, the steepness of the curvature of the lens 10 has been exaggerated. In actuality, the difference between the radii of curvature $R_F$ and $R_P$, as well as the difference between the lens diameters $d_F$ and $d_P$, would be almost imperceptible.

Figure 4:
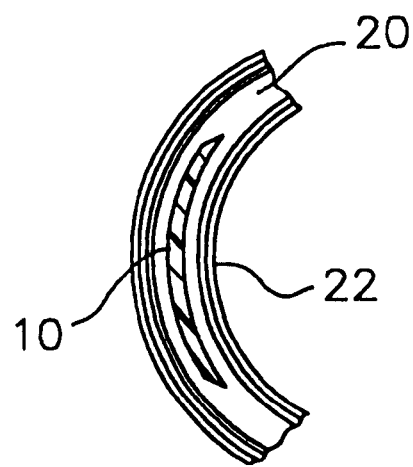
FIG. 4 is an enlarged axial, cross-sectional view showing the partially hydrated lens of FIG. 3 immediately after implantation into the stroma of a cornea.

FIG. 4 shows the partially hydrated lens 10, immediately after having been implanted into the stromal bed 20 of a cornea 22 using prior art surgical techniques. Specifically, a small incision was made in the cornea 22 to make a flap or hinge (not shown), which was then folded back to expose the middle layer of corneal tissue known as the stromal bed 20. The lens 10 was then placed on the stroma 20 and the flap returned to its initial position and smoothed over the lens 10.

Figure 5:
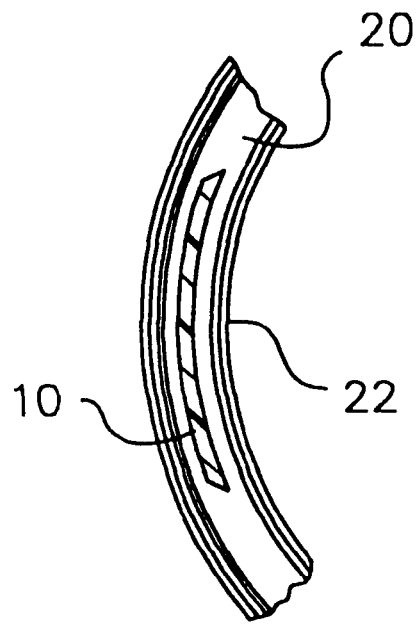
FIG. 5 is an enlarged axial, cross-sectional view, similar to FIG. 4, showing the implanted lens in its equilibrium state.

Initially, the partially hydrated lens 10 is more steeply curved than the cornea. In addition, the lens 10 may be slightly off-center with respect to the cornea 22. However, the difference in hydration between the lens 10 and the cornea creates an osmotic pressure gradient, causing the lens 10 to absorb water from the cornea 22 until a state of equilibrium is reached. As the lens 10 gradually absorbs water, it expands and flattens until it adheres to the stromal bed, centering itself as it flattens. After it centers and adheres, the lens 10 becomes fully hydrated and assumes a configuration substantially conforming to the curvature of the cornea 22, as shown in FIG. 5.

While this invention has been described with respect to various specific examples and embodiments, it is to be understood that the invention is not limited thereto and that it can be variously practiced within the scope of the following claims. For example, the partially hydrated state of the lens 10 could be achieved by fully hydrating the lens with a conventional isotonic solution, and then either air drying the lens 10 for a prescribed time period, or treating the lens 10 with a dehydrating agent. In some instances, such methods may be preferred, since a fully hydrated lens is more easily inspected for imperfections than a partially hydrated one.

In addition, while the intra-corneal implants and methods disclosed herein are believed to be particularly effective for treating hyperopia, the teachings of the foregoing disclosure could well be adapted to lenses for correcting myopia, astigmatism and other refractive errors, without departing from the spirit of the invention.

What is claimed is:

1. An intra-corneal implant comprising:

a lens structured to be implanted in a cornea and comprising a hydrophilic polymeric material;

the lens having an initial state prior to implantation into the cornea wherein the lens is partially hydrated and is more steeply curved than a central portion of the cornea, the lens being structured to be further hydrated after implantation into the cornea to a final state in which the lens assumes a flatter shape than the lens in the partially hydrated state.

2. The intra-corneal implant according to claim 1, wherein the lens in the final state has a curvature closely conforming to a substantially uniformly curved central area of a corneal stroma.

3. The intra-corneal implant according to claim 1, wherein the lens in the partially hydrated state has a first imbibition pressure causing the lens to absorb water from the cornea when implanted therein, and the lens in the final hydrated state has a second imbibition pressure causing the lens to substantially cease absorbing water from the cornea.

4. The intra-corneal implant according to claim 1, wherein the partially hydrated lens comprises an amount of fluid selected to create an osmotic pressure relative to stromal fluids in the cornea when the partially hydrated lens is implanted in the stroma of the cornea, the osmotic pressure gradient causing enhanced adhesion of the lens to the stroma.

5. The intra-corneal implant according to claim 1, in combination with means for maintaining the lens in the partially hydrated state prior to implantation in a cornea.

6. The combination according to claim 5, wherein the means for maintaining the lens in the partially hydrated state comprises a hypertonic hydration medium.

7. A packaging arrangement comprising:

a vessel containing a hypertonic hydration medium; and a lens stored in the hydration medium for implantation in a cornea, wherein the lens is formed of a hydrophilic polymeric material.

the hydration medium having a tonicity such that the lens is in an initial state in which the lens is partially hydrated and is more steeply curved than a central portion of the cornea, the lens being structured to be further hydrated after implantation into the cornea to a final state in which the lens substantially conforms to the curvature of the central portion.

8. The packaging arrangement according to claim 7, wherein the hydration medium comprises an aqueous carrier and a tonicity adjusting agent.

9. The packaging arrangement according to claim 8, wherein the tonicity adjusting agent is selected from the group consisting of sodium chloride, potassium chloride, sodium phosphate monobasic, sodium phosphate dibasic and combinations thereof.

10. The packaging arrangement according to claim 7, wherein the lens is stored in a partially hydrated state.

11. The packaging arrangement according to claim 10, wherein the lens is expandable from the partially hydrated state to the final hydrated state.

12. A method for treating refractive errors in the cornea of an eye, comprising:

of implanting a partially hydrated lens in a cornea, the lens being more steeply curved than a central portion of the cornea;

causing the lens to absorb water from the cornea so as to flatten the lens:

allowing the lens to self-center within the cornea.

13. The method according to claim 12, wherein the lens has an imbibition pressure that causes the lens to absorb water when implanted in the cornea.

14. The method according to claim 13, wherein the lens expands to an equilibrium state as it absorbs water from the cornea, the lens substantially ceasing to absorb water when in the equilibrium state.

15. The method according to claim 14, wherein:

the lens in the equilibrium state has a curvature closely conforming to a substantially uniformly curved central area of a cornea;

the partially hydrated lens is more steeply curved than the lens in the equilibrium state; and the lens flattens while expanding into the equilibrium state, centering itself on the central area of the cornea as it flattens.

16. The method according to claim 12, wherein the partially hydrated lens comprises an amount of fluid selected to create an osmotic pressure gradient against stromal fluids when the partially hydrated lens is implanted in the stroma of a cornea, the osmotic pressure gradient causing enhanced adhesion of the lens to the stroma.

17. The method according to claim 12, comprising wetting a prehydrated lens to a partially hydrated state prior to the step of implanting the pre-hydrated lens in the cornea.

18. The method according to claim 17, wherein of wetting a pre-hydrated lens to a partially hydrated state comprises soaking the pre-hydrated lens in a hypertonic solution.

19. The method according to claim 12, further comprising allowing the lens to adhere to the cornea.

* * * * *